(12) United States Patent
Chiu et al.

(10) Patent No.: US 6,761,708 B1
(45) Date of Patent: Jul. 13, 2004

(54) RADIOPAQUE MARKER FOR A CATHETER AND METHOD OF MAKING

(75) Inventors: Jessica G. Chiu, Belmont, CA (US); Arlene S. Yang, Redwood City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 115 days.

(21) Appl. No.: 09/703,518

(22) Filed: Oct. 31, 2000

(51) Int. Cl.[7] .................. A61M 25/00; A61M 31/00
(52) U.S. Cl. ............... 604/265; 604/103.1; 606/194
(58) Field of Search .............. 606/194; 600/426; 623/1.34, 1.11, 1.12; 604/265, 103.1

(56) References Cited

U.S. PATENT DOCUMENTS

| | | | |
|---|---|---|---|
| 4,952,357 A | 8/1990 | Euteneuer | 264/129 |
| 5,506,059 A | 4/1996 | Robbins et al. | 428/457 |
| 5,520,664 A | 5/1996 | Bricault, Jr. et al. | 604/265 |
| 5,607,463 A | 3/1997 | Schwartz et al. | 623/1 |
| 5,609,606 A | 3/1997 | O'Boyle | 606/194 |
| 5,797,868 A | 8/1998 | Leone | 604/21 |
| 5,858,556 A * | 1/1999 | Eckert et al. | 148/521 |
| 5,873,904 A * | 2/1999 | Ragheb et al. | 604/265 |
| 5,919,126 A * | 7/1999 | Armini | 600/3 |
| 5,991,650 A * | 11/1999 | Swanson et al. | 600/372 |
| 6,210,396 B1 * | 4/2001 | MacDonald et al. | 604/103.1 |
| 6,315,794 B1 * | 11/2001 | Richter | 623/1.34 |

* cited by examiner

Primary Examiner—Gary Jackson
(74) Attorney, Agent, or Firm—Fulwider Patton Lee & Utecht, LLP.

(57) ABSTRACT

A catheter having a radiopaque marker and a method of forming the radiopaque marker on the catheter component. One embodiment of the invention is directed to a method of making a radiopaque marker on a catheter component comprising depositing a first layer of radiopaque material onto at least a section of the catheter component, which in a presently preferred embodiment is deposited by thin film deposition, and electroplating a second layer of radiopaque material onto an outer surface of the first layer of radiopaque material. In one embodiment of the invention, a catheter component has a radiopaque marker comprising a first layer of radiopaque material, and a second layer of radiopaque material on the first layer having a thickness greater than the thickness of the first layer. In another embodiment of the invention, a first layer of radiopaque material comprises a blend of polymeric material and radiopaque material and a second layer of radiopaque material is electroplated onto the blended first layer. The radiopaque marker of the invention may be on a variety of catheter components including a catheter shaft or a balloon on a balloon catheter.

24 Claims, 2 Drawing Sheets

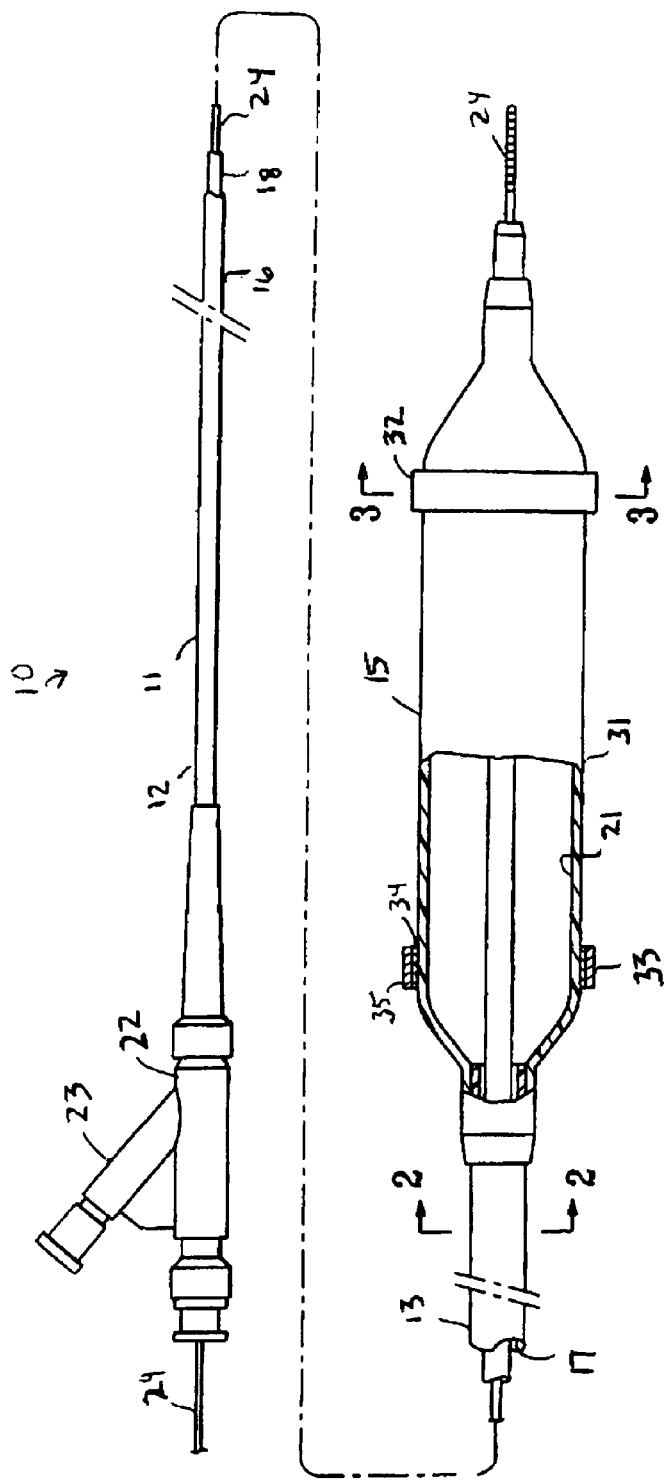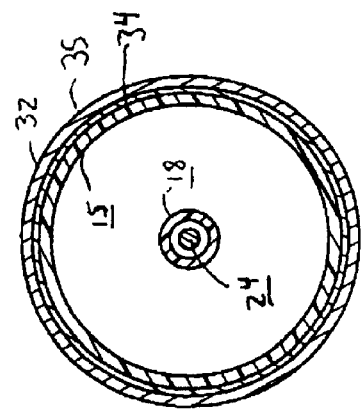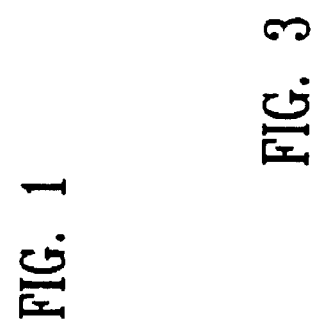

RADIOPAQUE MARKER FOR A CATHETER AND METHOD OF MAKING

BACKGROUND OF THE INVENTION

This invention generally relates to medical devices, and particularly to catheters for angioplasty and stent delivery.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of an dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairng or strengthening the dilated area. To reduce the restenosis rate and to strengthen the dilated area, physicians frequently implant an intravascular prosthesis, generally called a stent, inside the artery at the site of the lesion. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

Typically, the distal section of a balloon catheter or other percutaneous device will have a radiopaque marker which the operator of the device can see under x-ray or fluoroscopy imaging. Generally, a band or ring of solid radiopaque metal is secured about an inner or outer shaft of a balloon catheter to serve as a radiopaque marker. Such a configuration may add stiffness and discontinuity to the catheter shaft as the solid metal bands are relatively inflexible compared to a polymeric balloon catheter shaft. There are several methods for adhering radiopaque metal materials to a catheter component. However, processes which expose polymeric catheter components to relatively high temperatures may melt or otherwise adversely affect the performance characteristics of the component. What has been needed is a radiopaque marker for intracorporeal devices with improved performance characteristics.

SUMMARY OF THE INVENTION

The invention is directed to a catheter having a radiopaque marker, and a method of making a radiopaque marker on a catheter component in which an outer layer of radiopaque material is electroplated onto an inner layer of radiopaque material. In one embodiment of the invention, a catheter component has a radiopaque marker having a first layer of radiopaque material, and a second layer of radiopaque material on the first layer with a thickness greater than the thickness of the first layer. In one embodiment of the invention, a radiopaque marker has a first layer of radiopaque material formed of a blend of polymeric material and radiopaque material, and a second layer of radiopaque material electroplated onto the blended first layer. A method of making a radiopaque marker on a catheter component generally involves depositing a first layer of radiopaque material onto at least a section of the catheter component, which in a presently preferred embodiment is deposited by thin film deposition, and electroplating a second layer of radiopaque material onto an outer surface of the first layer of radiopaque material. In one embodiment, the catheter component having the radiopaque marker is a balloon on a balloon catheter. However, the radiopaque marker of the invention may be on a variety of catheter components including a catheter shaft.

In one embodiment, the first layer of radiopaque material is applied by a thin film deposition technique, such as chemical vapor deposition (CVD), or physical vapor deposition (PVD). Specifically, PVD methods useful in the method of the invention include sputtering, and ion beam assisted deposition (IBAD) which is a vacuum deposition process combining PVD and ion beam bombardment available from Spire Corporation. In CVD, a chemical reaction in the vapor phase of a gas stream produces a compound which is deposited downstream onto a substrate. In PVD, energy applied to a target removes material from the target as a vapor which is deposited onto a substrate. A presently preferred method of applying the first layer of radiopaque material involves sputtering, in which a target formed of the radiopaque material is bombarded with energetic electrons and the resulting vaporized material is deposited onto the surface of the catheter component.

The radiopaque marker must be sufficiently thick to provide adequate radiopacity under fluoroscopy. During thin film deposition of radiopaque material, thicker layers of deposited radiopaque material formed using longer processing times result in the catheter component being exposed to higher temperatures. One embodiment of the invention minimizes or avoids damage to the catheter component caused by exposure to high temperatures by minimizing the thickness of the first layer applied by thin film deposition, and electroplating a second layer of radiopaque material onto the first layer.

The first layer of radiopaque material is deposited onto the catheter component in a sufficiently short period of time to avoid adversely and excessively heating the catheter component. However, the first layer of radiopaque material has sufficient conductivity to allow the second layer of radiopaque material to be electroplated onto the first layer. Additionally, the first layer of radiopaque material is sufficiently thick to substantially lower the process time required to complete the radiopaque marker by electroplating the second layer. In one embodiment of the invention, the first layer and second layers of radiopaque material are selectively applied to the catheter component, i.e., the layers have a length less than the length of the catheter component. In one embodiment, the radiopaque markers have a length substantially less than the length of the catheter component. In the embodiment in which the catheter component is a balloon, the radiopaque marker having a length substantially less than the balloon length has a length not more than about 2% to about 10%, preferably about 2% to about 5% of the balloon length. In the embodiment in which the catheter component is a catheter shaft, the radiopaque marker having a length substantially less than the shaft length has a length not more than about 0.005% to about 0.05%, preferably about 0.006% to about 0.04% of the shaft length. A mask may be used on portions of the catheter component, so that only a desired section of the component is exposed during the thin film deposition of the first layer.

Variables such as the radiopaque material type, particle size, and layer thickness may be varied to improve adhesion of the radiopaque material layers. The radiopaque material used to form the first layer may be the same as or different from the radiopaque material forming the second layer, and a variety of suitable radiopaque materials may be used, including gold, tungsten, and platinum/iridium alloys. Any metal ions can be used as the first layer, to provide a substrate which attracts the radiopaque material of the second layer during the electroplating process used to form the second layer, but are preferably a highly radiopaque material. The radiopaque materials are preferably easily deposited and relatively soft. A presently preferred material for the first and second layer is gold. The first and second layers may be formed of materials having different particle sizes.

Any number of radiopaque markers of the invention can be secured to a component of the catheter, such as the catheter balloon or catheter shaft, having the same or varied configurations. In embodiments of the invention where a plurality of radiopaque markers are secured to the catheter, the markers may be spaced at regular intervals in order to provide a measuring function. Additionally, the markers may provide a visualization function by marking features of interest of the balloon catheter, such as proximal and distal ends of the balloon, rapid exchange ports, or a distal extremity of the catheter. In a presently preferred embodiment, the markers are applied to the proximal and distal ends of the working length of a balloon which has been formed by blow molding. In one embodiment, the radiopaque marker of the invention is provided on a shaft inner tubular member when, for example, possible damage to the patient's vessel from a marker located on an outer surface of the catheter could occur.

The radiopaque markers of the invention applied to a surface of a balloon are particularly useful in balloon catheters having an opaque balloon. Specifically, during assembly of the catheter, radiopaque markers on the inner tubular member must be correctly aligned at either end of the balloon working length. This procedure is complicated by the opaque balloon which obscures the view of the markers. Additionally, a catheter inner tubular member which is present only to provide a place for the radiopaque markers can be eliminated where the radiopaque markers of the invention are applied to a surface of the balloon.

The method of the invention avoids damage to the catheter component caused by exposure to high temperatures, due to the first layer of radiopaque material applied by thin film deposition and the second layer of radiopaque material applied by electroplating. As a result, unreasonably long process cycle times required to apply a thick radiopaque marker solely by thin film deposition are avoided. Moreover, the radiopaque markers of the invention can be applied to a surface of the balloon without damaging the balloon, despite the thinness of the balloon wall and the need for strictly controlled balloon dimensions. Additionally, the radiopaque markers of the invention may be made thinner than conventional marker bands which are formed of a machined metal ring. Machined metal ring markers have a thickness lower limit equal to the minimum wall thickness required to draw the metal tubing that forms the conventional marker bands, which is not required in the radiopaque markers of the invention.

These and other advantages of the invention will become more apparent from the following detailed description when taken in conjunction with the accompanying exemplary drawings.

BRIEF DESCRIPTION OF THE DRAWINGS

FIG. 1 is an elevational view, partially in section, of a balloon catheter having radiopaque markers embodying features of the invention.

FIG. 2 is a transverse cross-section of the catheter shown in FIG. 1 taken at line 2—2.

FIG. 3 is a transverse cross-section of the catheter shown in FIG. 1 taken at line 3—3.

DETAILED DESCRIPTION OF THE INVENTION

Figure 6:
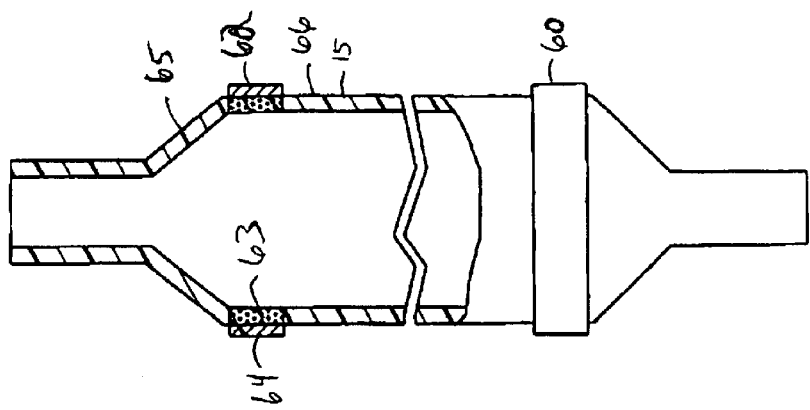
FIG. 6 is an elevational view, partially in section, of an alternative embodiment which embodies features of the invention, in which the radiopaque marker comprises a first layer formed of a blend of polymeric and radiopaque material and a second layer of radiopaque material electroplated onto the first layer.

FIG. 1 illustrates an embodiment of an intraluminal catheter 10 of the invention, generally comprising an elongated shaft 11 having a proximal end 12 and a distal end 13, and a balloon 15 on a distal shaft section. In the embodiment illustrated in FIG. 1, the shaft 11 comprises an outer tubular member 16 defining an inflation lumen 17, and an inner tubular member 18 disposed within the outer tubular member and defining a guidewire lumen 19 (FIG. 2) configured to slidably receive a guidewire. In the illustrated embodiment, the coaxial relationship between outer tubular member 16 and inner tubular member 18 defines annular inflation lumen 17. Balloon 15 has a proximal end sealingly secured to the distal end of outer tubular member 16 and a distal end sealingly secured to the distal end of inner tubular member 18, so that its interior 21 is in fluid communication with inflation lumen 17. Adapter 22 at the proximal end of the shaft 11 is configured to direct inflation fluid through arm 23 into inflation lumen 17, and provide access to guidewire lumen 19. Guidewire 24 is disposed within guidewire lumen 19. FIGS. 2 and 3 illustrate transverse cross sections of the balloon catheter 10 shown in FIG. 1, taken along lines 2—2 and 3—3, respectively.

Balloon 15 has a working length 31, a distal radiopaque marker 32 at a distal end of working length 31, and a proximal radiopaque marker 33 at a proximal end of the balloon working length 31. In an alternative embodiment, the number and location of the markers may be different, such as, for example, a balloon catheter having a single radiopaque marker located at the center of the balloon working length 31 (not shown). Each radiopaque marker 32/33 comprises a first layer of radiopaque material 34 on an outer surface of the balloon 15 applied by deposition onto the balloon, and a second layer of radiopaque material 35 electroplated onto the first layer 34. Although radiopaque markers 32/33 are illustrated on balloon 15, it should be understood that the radiopaque markers of the invention may be applied to a variety of catheter components including the catheter shaft, such as for example on the inner tubular member 18 aligned with the ends or the center of the balloon working length as discussed above.

In the embodiment illustrated in FIG. 1, the second layer of radiopaque material 35 has a thickness greater than the thickness of the first layer 34, and the length of the second layer of radiopaque material 35 is the same as the length of the first layer of radiopaque material 34. Although radiopaque material layers 34/35 are illustrated as single layers, in an alternative embodiment, each layer 34/35 may comprise multiple thinner layers of the radiopaque material successively applied one on top of the other. The thickness of the first layer 34 on balloon 15,is about 0.00005 inch to about 0.00025 inch, preferably about 0.0001 inch to about 0.00025 inch, and the thickness of the second layer 35 is about 0.00075 inch to about 0.001 inch, preferably about 0.00075 inch to about 0.0009 inch. In the embodiment illustrated in FIG. 1, first and second layers 34/35 are formed of different materials. In alternative embodiments, the first and second layers 34/35 are formed of the same materials or of materials having different particle sizes (not shown).

In the embodiment of FIG. 1, the radiopaque markers 32/33 are selectively applied to the balloon outer surface, so that they each have a length substantially less than a length of the working length 31 of the balloon 15. In the embodiment of FIG. 1, the length of the radiopaque marker is not more than about 2% to about 15% of the working length of the balloon. In a presently preferred embodiment, the length of the radiopaque marker 32/33 is about 0.05 mm to about 1.5 mm, for a balloon having a total length of about 10 mm to about 70 mm and a working length of about 8 mm to about 60 mm.

Figure 4:
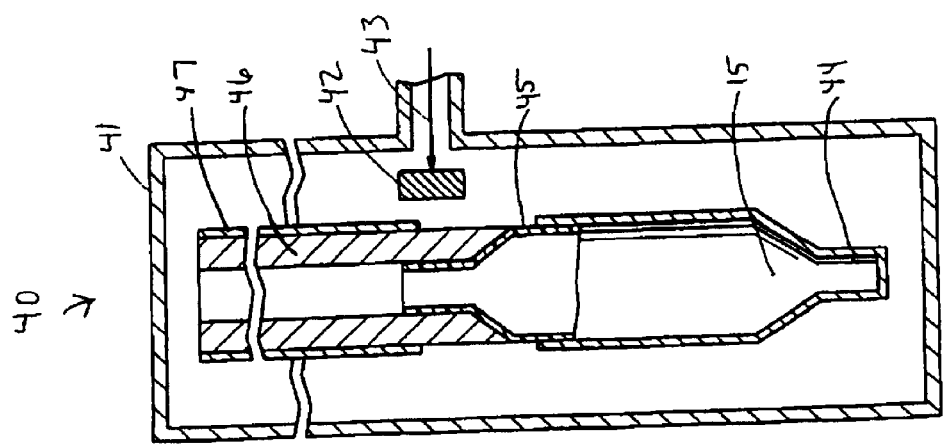
FIG. 4 is an elevational view, partially in section, of a vapor deposition apparatus useful in a method which embodies features of the invention, illustrating a balloon for a catheter within the vapor deposition apparatus chamber for deposition of a first layer of radiopaque material thereon.

FIG. 4 illustrates an elevational view of a vapor deposition apparatus 40 useful in a method of depositing radiopaque material which embodies features of the invention. The vapor deposition apparatus 40 generally comprises a vapor deposition chamber 41 and a target formed of radiopaque marker material 42 in communication with the chamber. An energy source, such as energetic electrons 43, is directed toward the radiopaque material target 42, to form vaporized radiopaque material which deposits on the exposed surfaces of balloon catheter 10 in the vapor deposition chamber 41. Removable mask 44 covers sections of the balloon 15, to prevent the deposition of radiopaque material on the covered sections of the balloon. Consequently, the first layer of radiopaque material 34 is formed from vaporized radiopaque material deposited onto the exposed section 45 of the balloon. In the embodiment illustrated in FIG. 4, removable fixture 46 is provided on the proximal end of the balloon 15 as a handle for holding onto the balloon. Fixture 46 is a tubular member, which releasably attaches to the balloon as for example by a frictional fit or clamp. Fixture 46 may be formed of a variety of suitable materials including polymeric materials. In the embodiment illustrated in FIG. 4, a mask 47 on the fixture does not extend to the end of the fixture 46. Thus, a length of the fixture 46 is exposed, so that vaporized radiopaque material deposits onto the fixture 46 in a continuous layer longitudinally aligned with the radiopaque material deposited onto the exposed section 45 of the balloon. The radiopaque material deposited onto fixture 46 facilitates electroplating the second layer of radiopaque material 35 by increasing the amount and therefore the conductivity of the radiopaque material present during electroplating. In the embodiment in which first layer 34 extends onto fixture 46, the first layer 34 is typically cut as for example with a laser, or otherwise broken, at a point along the length of the layer 34 located at the junction between the fixture 46 and the balloon exposed section 45, so that the fixture 46 can be removed from the balloon when desired. Preferably, the deposition of the first layer 34 is completed in about 15 to about 45 minutes. The conductivity of the first layer is at least sufficient to allow the second layer to be electroplated thereon. In one embodiment, the first layer having a thickness of at least about 0.00005 inch to about 0.00025 inch has sufficient conductivity to allow the second layer to be electroplated thereon.

Figure 5:
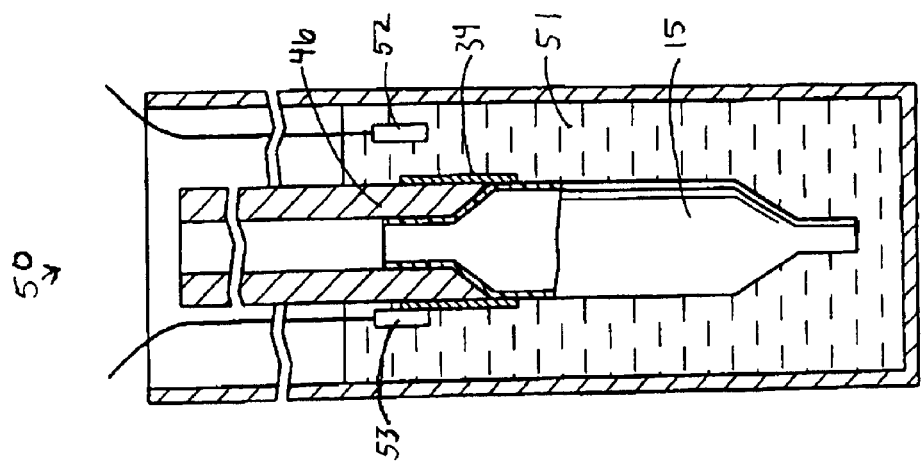
FIG. 5 is an elevational view, partially in section, of an electroplating apparatus useful in a method which embodies features of the invention, illustrating a balloon for a catheter within the electroplating apparatus for electroplating a second layer of radiopaque material on a first layer of radiopaque material.

FIG. 5 illustrates an electroplating apparatus 50 useful in a method of electroplating which embodies features of the invention. The electroplating apparatus 50 generally comprises a bath 51 containing the radiopaque ions, a first electrode 52 in the bath and a second electrode 53 in contact with first layer 34 on balloon 15. Balloon 15 having the first layer of radiopaque ionic material 34 deposited onto the balloon and onto fixture 46 is in bath 51. A potential difference is applied across the electrodes, which results in the radiopaque material in the bath being plated onto the first layer 34. As discussed above, in the embodiment in which the first layer 34 extends from the balloon 15 onto the fixture 46, the radiopaque material vapor deposited onto the fixture 46 increases the amount of radiopaque material present as a primer layer onto which second layer 35 is electroplated, which thus provides increased conductivity in the first layer for electroplating second layer onto first layer 34. Alternatively, during electroplating of the second layer 35, the first layer 34 may be provided only on the balloon 15, and not on the fixture 46. The first layer 34 may be provided only on the balloon by, for example, providing a mask 47 on the fixture which extends over the entire length of the fixture 46 so that no outer surface of the fixture 46 is exposed during deposition of the first layer 34, or a different fixture may be used to hold the balloon 15 during, electroplating of the second layer 35. Balloon 15 may be fully or partially inflated during application of the first and/or second layer 34/35. After second layer 35 is electroplated, the balloon 15 is removed from the bath 51, and the fixture 46 is removed from the balloon, leaving first layer 34 and second layer 35 of radiopaque material on section 45 of balloon 15. Preferably the electroplating is completed in less than about 1 hour, and most preferably in about 2 to about 5 minutes.

In an alternative embodiment illustrated in FIG. 6, balloon 15 has distal radiopaque marker 60 and proximal radiopaque marker 62, the markers 60/62 comprise a first layer of radiopaque material 63 formed of a blend of a polymeric material and a radiopaque material, and a second layer of radiopaque material 64 electroplated onto first layer 63. The radiopaque first layer 63 can be formed by doping a radiopaque material into a section of the catheter component such as balloon 15 or catheter shaft tubing, which corresponds to the dimensions of the radiopaque marker 60/62. The radiopaque material doped into the polymeric material is preferably platinum/iridium or gold. The radiopaque material may be in powder or particulate form which is mixed with the polymer material of the balloon 15 before extrusion of a polymeric tube which forms balloon 15. In the illustrated embodiment, the first layer 63 is joined between and to a first section 65 of the balloon and a second section 66 of the balloon which is longitudinally disposed from the first section 65. Alternatively, the radiopaque marker 64 may be formed from a separate discrete member such as a ring of polymeric material having radiopaque material blended therein, which is preformed and subsequently secured to an outer surface of the balloon 15 or between adjacent sections of the balloon. Because the doped section is localized on a small section of the balloon, the doped section may have a relatively high concentration of radiopaque material without adversely affecting balloon performance characteristics such as the strength of the balloon. In the embodiment of the invention where the radiopaque first layer 63 is formed from a separate discrete member, the first layer 63 may be secured to the balloon 15 by a variety of suitable methods including an adhesive bond, a solvent bond, or heat fusing or shrinking of the radiopaque first layer 63 to the balloon 15. The polymeric material blended with the radiopaque material to form first layer 63 may be the same as or different from the polymeric material forming balloon 15, and is preferably compatible with the balloon material. The polymeric material may have a Shore Durometer hardness which is less than, greater than, or the same as the hardness of the material used to form balloon 15. In a presently preferred embodiment, the polymeric material is the same as the balloon material, and has a Shore Durometer hardness which is the same as the hardness of the balloon 15 material.

The dimensions of catheter 10 are determined largely by the size of the guidewires to be employed and the size of the artery or other body lumen through which the catheter must pass or the size of the stent being delivered. Typically, the outer tubular member 16 has an outer diameter of about 0.02 to about 0.04 inch (0.05 to 0.10 cm), usually about 0.032 inch (0.081 cm), an inner diameter of about 0.015 to about 0.03 inch (0.038 to 0.076 cm), usually about 0.029 inch (0.074 cm). The wall thickness of the outer tubular member 16 can vary from about 0.002 to about 0.008 inch (0.0051 to 0.0201 cm), typically about 0.003 inch (0.0076 cm). The inner tubular member 18 typically has an outer diameter of about 0.017 to about 0.023 inch (0.043 to 0.058 cm), usually about 0.020 inch (0.05 cm). The overall working length of the catheter 10 may range from about 100 to about 160 cm, and is typically about 145 cm. Preferably, balloon 15 may have a length about 8 mm to about 58 mm and typically about 20 mm, with an inflated working diameter of about 0.5 mm to about 7 mm and typically about 3 mm.

The balloon 15 may be formed of conventional catheter balloon materials, including polyamides such as nylon or PEBAX, and polyesters. Inner tubular member 18 and outer tubular member 16 can be formed by conventional techniques, for example by extruding, from materials already found useful in intravascular catheters such a polyethylene, polyvinyl chloride, polyesters, polyamides, polyimides and composite materials. The various components may be joined by heat bonding or use of adhesives.

Proximal and distal radiopaque markers on a balloon can be prepared according to the following example. Place a balloon having a working length of about 2 cm and an inflated diameter of about 3 mm in a vapor deposition chamber. A source material comprising gold or platinum is bombarded with an energy source comprising argon or krypton, for 1 to about 15 minutes at $10^{-3}$ Torr pressure at 250 Watts power to apply a first layer of radiopaque material having a thickness of about 0.002 mm to the balloon. Place the balloon in an electroplating bath comprising a 50% solution of gold or platinum in water, with an electrode in contact with the first layer of radiopaque material. A potential of about 20 mA is applied to the electrodes for about 15 minutes, to apply a second layer of radiopaque material having a thickness of about 0.02 mm to the first layer.

Although not illustrated, radiopaque markers 32/33 may be provided on a catheter shaft, as for example on various locations on inner tubular member 18 such as at either end of the balloon working length 31, at the center of the balloon working length 31, or from the proximal end to the distal end of the balloon working length 31. The thickness of the first layer 34 on inner tubular member 18 is about 0.00005 inch to about 0.00026 inch, preferably about 0.0001 inch to about 0.00025 inch, and the thickness of the second layer 35 is about 0.00075 inch to about 0.001 inch, preferably about 0.00075 inch to about 0.0009 inch.

The balloon catheter illustrated in FIG. 1 is an over-the-wire catheter. However, various balloon catheter designs may be used, such as rapid exchange and fixed wire catheters. Rapid exchange catheters typically have an elongated shaft with a proximal end, a distal end with a balloon on a distal shaft section in fluid communication with an inflation lumen, a distal port in the distal end of the catheter, a proximal port spaced a substantial distance from the proximal end of the catheter closer to the distal end than to the proximal end, and a short guidewire lumen extending between the proximal and distal ports.

While the present invention is described herein in terms of certain preferred embodiments, those skilled in the art will recognize that various modifications and improvements may be made to the invention without departing from the scope thereof. For example, while the invention is illustrated primarily in terms of radiopaque markers on either end of the working length of a balloon, the markers of the invention may be applied to various locations on the catheter or other medical device. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. An intraluminal catheter having a polymeric component having at least one radiopaque marker, the radiopaque marker comprising:
   a) a first layer of radiopaque material; and
   b) a second layer of radiopaque material on the first layer, having a thickness greater than a thickness of the first layer.

2. The catheter of claim 1 wherein the first layer of radiopaque material comprises a deposited layer of radiopaque material on an outer surface of the polymeric catheter component, and the second layer of radiopaque material comprises an electroplated layer of radiopaque material on an outer surface of the first layer of radiopaque material.

3. The catheter of claim 1 wherein the second layer or radiopaque material extends the entire length of the first layer.

4. The catheter of claim 1 wherein the first and second layers of radiopaque material are formed of the same radiopaque material.

5. The catheter of claim 1 wherein the first layer of radiopaque material has a smaller particle size than the second layer of radiopaque material.

6. The catheter of claim 1 wherein the first layer of radiopaque material comprises a first radiopaque material and the second layer of radiopaque material comprises a second radiopaque material different from the first radiopaque material.

7. The catheter of claim 1 wherein the first layer of radiopaque material comprises a blend of a polymeric material and radiopaque material.

8. The catheter of claim 7 wherein the second layer comprises an electroplated layer of radiopaque material on the blended first layer.

9. The catheter of claim 7 wherein the polymeric catheter component comprises a first section longitudinally spaced from a second section adjacent thereto, and the first layer of radiopaque material is joined to and extends between the longitudinally spaced sections.

10. The catheter of claim 1 wherein the polymeric catheter component is a catheter shaft.

11. The catheter of claim 1 wherein the polymeric catheter component is an inflatable balloon.

12. The catheter of claim 11 having a distal radiopaque marker at a distal end of a working length of the balloon and a proximal radiopaque marker at a proximal end of the working length of the balloon, the proximal and distal radiopaque markers each comprising a first layer of radiopaque material, and a second layer of radiopaque material on the first layer having a thickness greater than a thickness of the first layer.

13. The catheter of claim 11 wherein each of the distal and proximal radiopaque markers have a length substantially less than a length of a working length of the balloon.

14. The catheter of claim 1 wherein the thickness of the first layer is about 0.001 mm to about 0.01 mm.

15. The catheter of claim 1 wherein the thickness of the second layer is about 0.02 mm to about 0.025 mm.

16. The catheter of claim 1 wherein the second layer has a length of about 0.05 mm to about 1.5 mm.

17. A balloon catheter, comprising:
  a) an elongated catheter shaft, having a proximal end, a distal end, and a lumen;
  b) a balloon on a distal section of the catheter shaft, having a working length; and
  c) at least one distal radiopaque marker on an outer surface of the balloon at a distal end of the working length of the balloon and a proximal marker on the balloon outer surface at a proximal end of the working length of the balloon, the distal and proximal radiopaque markers comprising a first layer of radiopaque material, and a second layer of radiopaque material on the first layer having a thickness greater than a thickness of the first layer.

18. A method of making a radiopaque marker for a polymeric catheter component, comprising:
  a) depositing a first layer of radiopaque material onto at least a section of the polymeric catheter component; and
  b) electroplating a second layer of radiopaque material onto an outer surface of the first layer of radiopaque material.

19. The method of claim 18 including depositing the first layer by thin film deposition.

20. The method of claim 18 wherein the first layer is deposited by a thin film deposition technique selected from the group consisting of chemical vapor deposition and physical vapor deposition.

21. The method of claim 18 including depositing the first layer of radiopaque material onto a section of the polymeric catheter component having a length substantially less than a length of the polymeric catheter component.

22. The method of claim 18 wherein the polymeric catheter component is a balloon and including electroplating onto the first layer a thicker layer of radiopaque material than the first layer of radiopaque material, to form the second layer.

23. The method of claim 18 wherein the polymeric catheter component is a catheter shaft and including electroplating onto the first layer a thicker layer of radiopaque material than the first layer of radiopaque material, to form the second layer.

24. The method of claim 18 wherein depositing the first layer comprises depositing a layer having a thickness of about 0.001 mm to about 0.01 mm, and electroplating the second layer comprises electroplating a layer having a thickness of about 0.2 mm to about 0.025 mm.

* * * * *